United States Patent
Lin et al.

(10) Patent No.: US 8,047,050 B2
(45) Date of Patent: Nov. 1, 2011

(54) PERFORMANCE TEST APPARATUS AND IMAGE TAKING DEVICE THEREOF

(75) Inventors: Yi-Hong Lin, Pingtung County (TW); Yei-Zhe Huang, Pingtung County (TW); Bo-Zhou Liao, Pingtung County (TW)

(73) Assignee: National Pingtung University of Science and Technology, Pingtung County (TW)

( * ) Notice: Subject to any disclaimer, the term of this patent is extended or adjusted under 35 U.S.C. 154(b) by 381 days.

(21) Appl. No.: 12/418,704

(22) Filed: Apr. 6, 2009

(65) Prior Publication Data
US 2010/0050732 A1    Mar. 4, 2010

(30) Foreign Application Priority Data

Sep. 1, 2008  (TW) .............................. 97133511 A

(51) Int. Cl.
*G01N 3/52* (2006.01)
*G01N 3/30* (2006.01)
*A63B 57/00* (2006.01)
(52) U.S. Cl. ..................... 73/12.02; 73/12.01; 73/12.09; 473/199; 473/222; 473/232; 473/257
(58) Field of Classification Search .................. 473/199, 473/198, 221, 222, 225, 231, 233, 234, 257; 73/12.02, 12.01, 12.04, 12.07, 12.09, 12.12, 73/12.14
See application file for complete search history.

(56) References Cited

U.S. PATENT DOCUMENTS

| | | | |
|---|---|---|---|
| 6,923,039 B2 | 8/2005 | Bissonnette et al. | |
| 7,311,611 B2 | 12/2007 | Cameron et al. | |
| 7,503,858 B2 | 3/2009 | Cameron | |
| 2007/0060410 A1* | 3/2007 | Gobush | 473/140 |
| 2008/0102972 A1* | 5/2008 | Lindsay | 473/251 |
| 2008/0287207 A1* | 11/2008 | Manwaring | 473/199 |
| 2010/0151957 A1* | 6/2010 | Hohla et al. | 473/221 |

* cited by examiner

*Primary Examiner* — Lisa Caputo
*Assistant Examiner* — Jonathan Dunlap
(74) *Attorney, Agent, or Firm* — Alan Kamrath; Kamrath & Associates PA

(57) ABSTRACT

A performance test apparatus includes a control unit, an image taking device, and a base having a table and a frame mounted to the table. The image taking device includes at least one image taker and at least one parallel light source. The at least one image taker is movably mounted to the frame and electrically connected to the control unit. The at least one parallel light source faces the table and is electrically connected to the control unit. The least one parallel light source includes a plurality of spot light sources. The control unit controls on/off of the at least one parallel light source, so that the at least one parallel light source flickers at a high frequency.

10 Claims, 8 Drawing Sheets

PERFORMANCE TEST APPARATUS AND IMAGE TAKING DEVICE THEREOF

BACKGROUND OF THE INVENTION

1. Field of the Invention

The present invention relates to a performance test apparatus and, more particularly, to a performance test apparatus for testing performance of balls and an image taking device of the performance test apparatus.

2. Description of the Related Art

Ball performance test apparatuses can test the performance and quality of a ball or a ball hitting member such as a golf club, and the test results can be utilized as reference data for designing the ball or golf club to improve the competitiveness.

Conventional ball performance test apparatuses include cannon type and robotic arm type. In the cannon type, an air compressor produces high-pressure air to blow a ball out of a cannon, and the ball hits a target at high speed to carry out a fatigue test of the striking face of the ball. In the robotic arm type, a robotic arm holds a ball hitting member such as a club or a bat and simulates a swinging motion of a man to hit a ball such as a golf ball, a table tennis ball, or a baseball, so as to measure the functional parameters of the ball or the ball hitting member, such as ball speed, ball spin, and the swaying angle of the club head. In both types, an image taking device is utilized to pick up images during the test. The image taking device is generally a high-speed camera having a flash light utilizing a spot light source and taking 10,000 pictures per second, so that the continuous images of the ball flying at high speed can be obtained. However, the high-speed camera is expensive, leading to a limitation of use of the ball performance test machines of these two types that are now only utilized on special tests. Furthermore, the illumination effect of the spot light source projecting in the path of the flying ball is not even in brightness, adversely affecting the measuring data of the ball.

Thus, a need exits for an inexpensive ball performance apparatus that can obtain precise data for improving the ball and the ball hitting member.

SUMMARY OF THE INVENTION

The primary objective of the present invention is to provide a performance test apparatus including at least one parallel light source that provides an image taking device with a light field with even brightness, improving measuring precision of the performance test apparatus.

Another objective of the present invention is to provide a performance test apparatus including a control unit to make the light field created by the at least one parallel light source flicker at high frequency, lowering the manufacturing costs and allowing wider application of the performance test apparatus.

A performance test apparatus according to the preferred teachings of the present invention includes a control unit, an image taking device, and a base having a table and a frame mounted to the table. The image taking device includes at least one image taker and at least one parallel light source. The at least one image taker is movably mounted to the frame and electrically connected to the control unit. The at least one parallel light source faces the table and is electrically connected to the control unit. The least one parallel light source includes a plurality of spot light sources. The control unit controls on/off of the at least one parallel light source, so that the at least one parallel light source flickers at a high frequency.

The present invention will become clearer in light of the following detailed description of illustrative embodiments of this invention described in connection with the drawings.

BRIEF DESCRIPTION OF THE DRAWINGS

The illustrative embodiments may best be described by reference to the accompanying drawings where.

Figure 1:
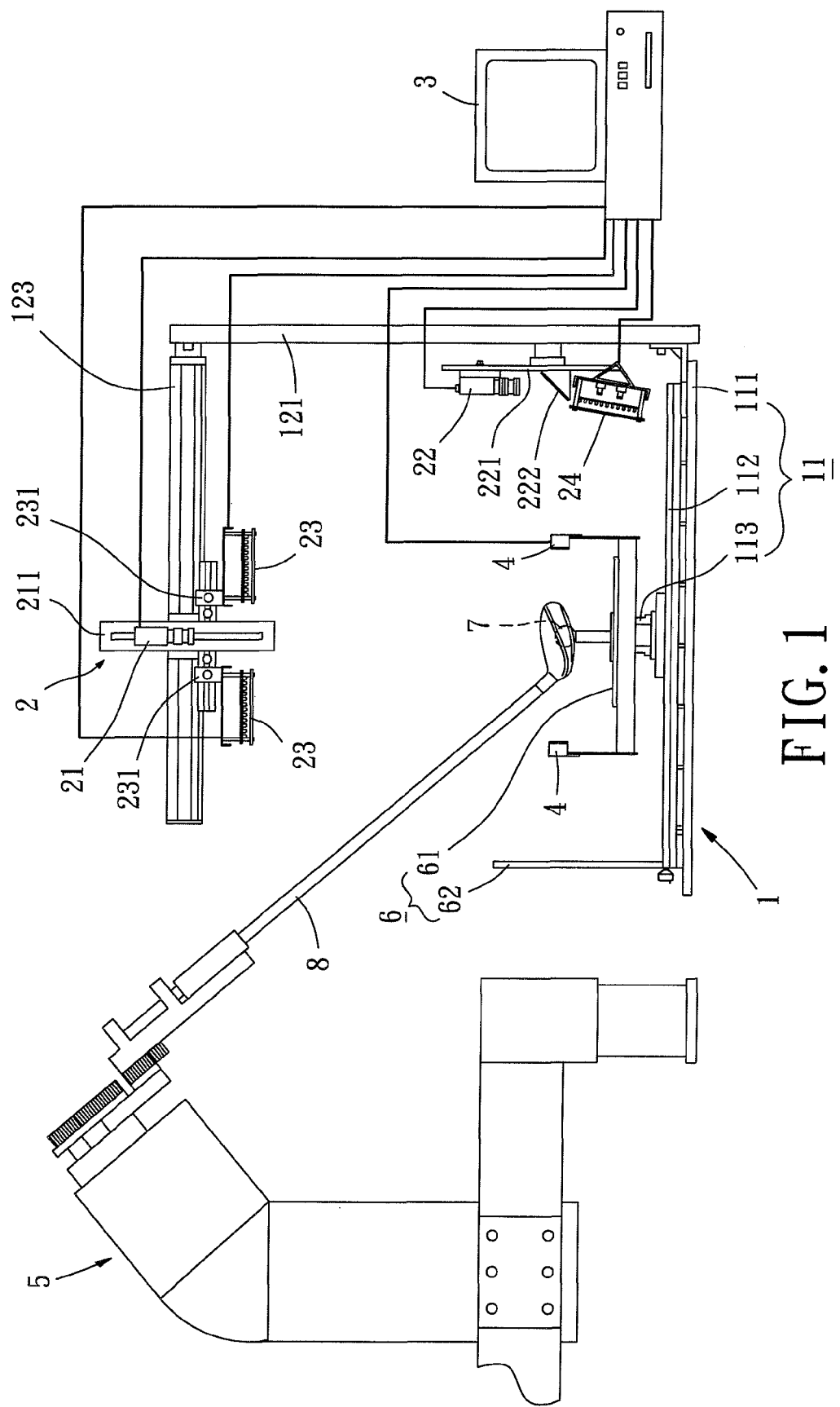
FIG. 1 shows a side view of a performance test apparatus according to the preferred teachings of the present invention.
Figure 2:
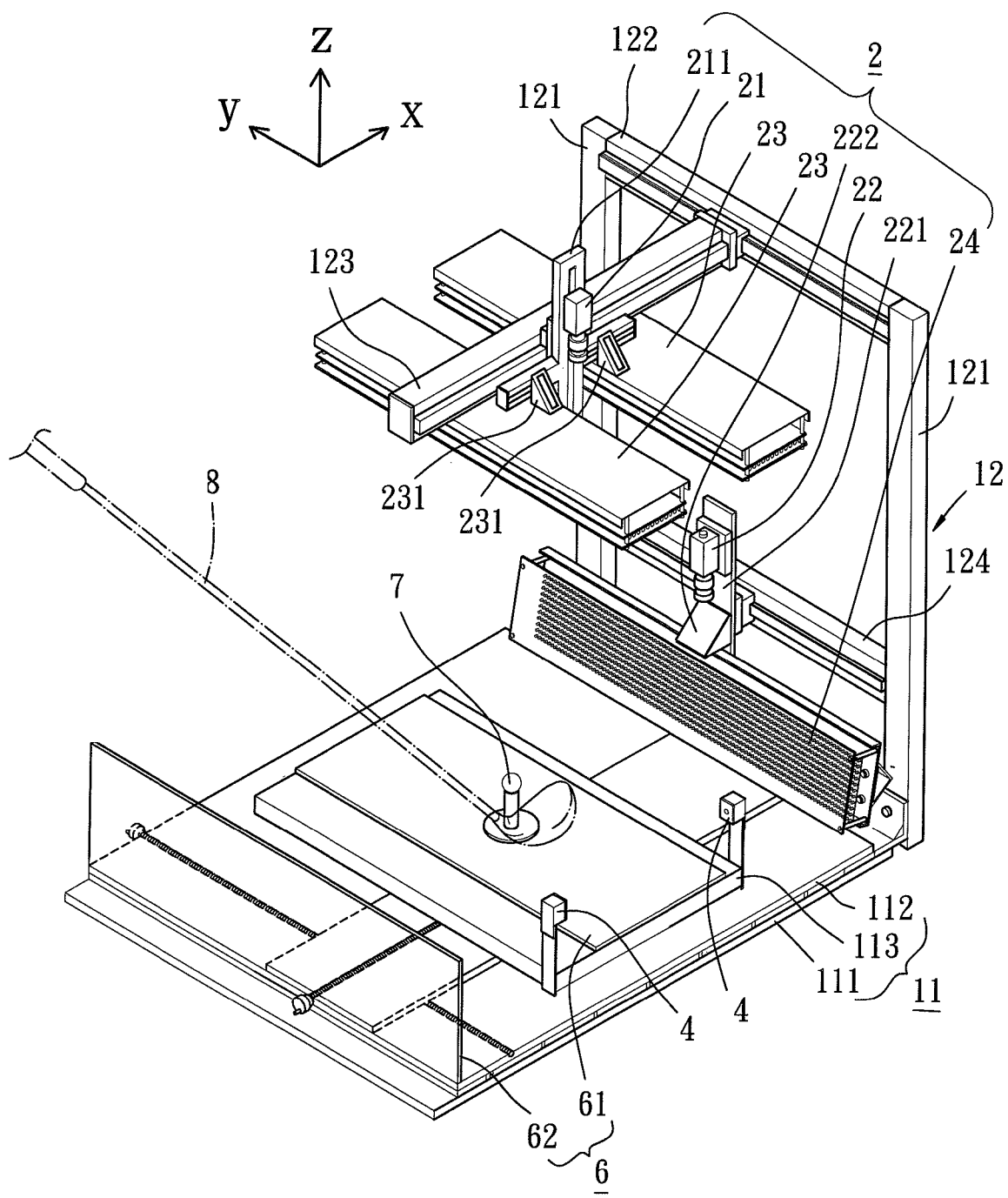
FIG. 2 shows a partial, perspective view of the performance test apparatus of FIG. 1.
Figure 3:
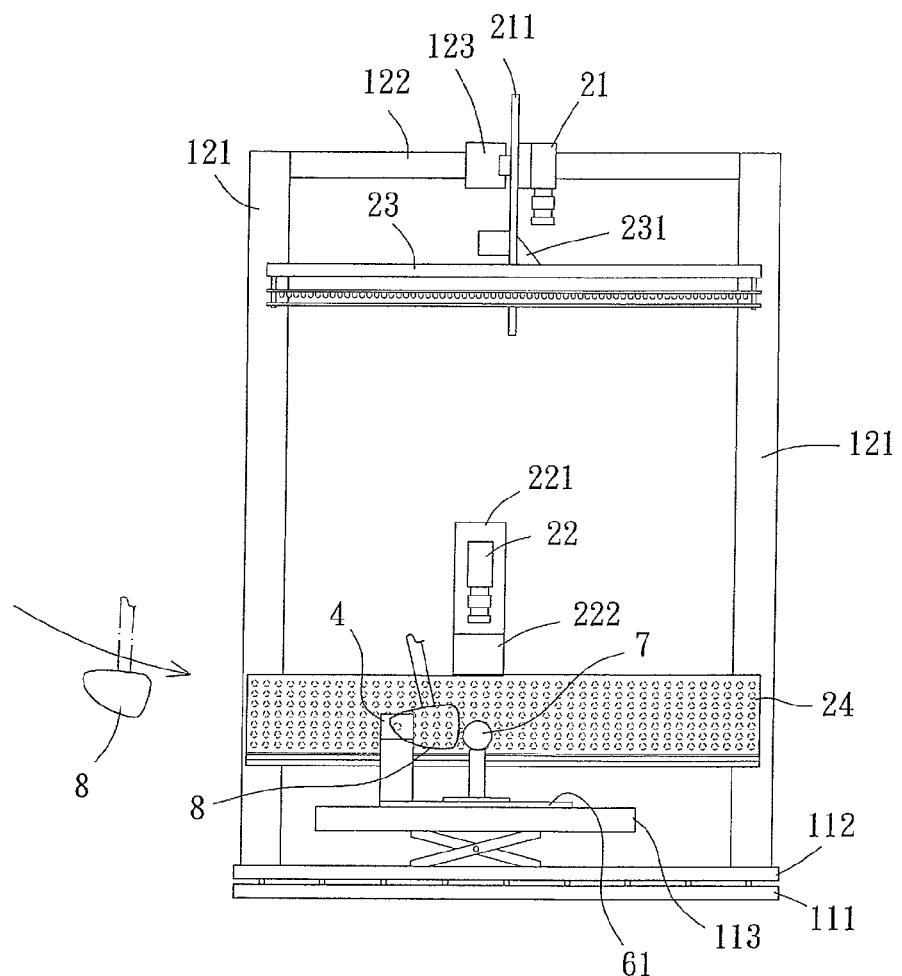
FIG. 3 shows a partial, side view of the performance test apparatus of FIG. 1.

All figures are drawn for ease of explanation of the basic teachings of the present invention only; the extensions of the figures with respect to number, position, relationship, and dimensions of the parts to form the preferred embodiments will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

Where used in the various figures of the drawings, the same numerals designate the same or similar parts. Furthermore, when the terms "first", "second", "third", "upper", "lower", "left", "right", "end", "section", "length", and similar terms are used herein, it should be understood that these terms have reference only to the structure shown in the drawings as it would appear to a person viewing the drawings and are utilized only to facilitate describing the invention.

DETAILED DESCRIPTION OF THE INVENTION

A performance test apparatus according to the preferred teachings of the present invention is shown in the drawings and generally includes a base 1, an image taking device 2, a control unit 3, a sensor 4, a swinging device 5, and a backdrop 6.

According to the preferred form shown, the base 1 is generally placed on a flat ground and includes a table 11 and a frame 12. The table 11 includes a fixed seat 111, a movable seat 112, and a holding seat 113. The fixed seat 111 carries other components of the base 1. The movable seat 112 is movably mounted on the fixed seat 111 and movable along a first axis Y. The holding seat 113 is movably mounted on the movable seat 112 and movable along a second axis X perpendicular to the first axis Y and along a third axis Z perpendicular to the first and second axes Y and X. The holding seat 113 holds a ball 7 to be tested. Although the ball 7 in the preferred form shown is a golf ball, the ball 7 can be any ball such as a golf ball, a tennis ball, or a table tennis ball that needs performance testing. By provision of the table 11, the ball 7 held by the holding seat 113 can be moved to a desired location relative to the fixed seat 111, so that the hitting spot of a striking face of a ball hitting member 8 hitting the ball 7 can be easily adjusted.

According to the preferred form shown, the frame 12 of the base 1 supports the image taking device 2 and includes two posts 121 and first, second, and third beams 122, 123, and 124. Each post 121 has an end fixed to a side of the fixed seat 111. The other end of each post 121 is coupled to two ends of the first beam 122. An end of the second beam 123 is movably coupled to the first beam 122, so that the second beam 123 is movable on the table 11 along the first axis Y. The third beam 124 is between the first beam 122 and the fixed seat 111 and includes two ends fixed to the posts 121.

According to the preferred form shown, the image taking device 2 includes a top-view image taker 21, a side-view image taker 22, two first parallel light sources 23, and a second parallel light source 24. The top-view image taker 21 and the side-view image taker 22 can be a couple-charged camera (CCD). The top-view image taker 21 picks up images of the trajectory of the ball 7 in a plane including the first and second axes Y and X, with the first parallel light sources 23 acting as the light source for the top-view image taker 21. The side-view image taker 22 picks up images of the trajectory of the ball 7 in another plane including the first and third axes Y and Z, with the second parallel light source 24 acting as the light source for the side-view image taker 22. Furthermore, the first and second parallel light sources 23 and 24 form a light field in which the holding seat 113 is located. Furthermore, the light field covers the flying area of the ball 7 that flies away from the holding seat 113 after it is hit. Each of the first and second parallel light sources 23 and 24 includes a plurality of spot light sources such as light-emitting diodes (LED) to provide even brightness throughout the light field.

According to the preferred form shown, the top-view image taker 21 is fixed on a first coupling member 211 that is movably mounted on the second beam 123. The first parallel light sources 23 are fixed on two connecting members 231 that are movably mounted to the first coupling member 211, with the first parallel light sources 23 located on two sides of the top-view image taker 21. Thus, the first parallel light sources 23 can move together with the top-view image taker 21 relative to the table 11 along the first and second axes Y and X. Furthermore, when the top-view image taker 21 is steady, the first parallel light sources 23 can move through a small travel along the second axis X.

According to the preferred form shown, the side-view image taker 22 is fixed on a second coupling member 221 on which the second parallel light source 24 is mounted. The second coupling member 221 is movably mounted on the third beam 124, so that the side-view image taker 22 and the second parallel light source 24 can move along the first axis Y. Note that the side-view image taker 22 is closer to the ball 7 than the top-view image taker 21 is. To obtain the same object distance for the top-view image taker 21 and the side-view image taker 22 and to avoid increasing of the length of the table 11 in the second axis X, a reflective mirror 222 is mounted below the side-view image taker 22 to reflect the image of the ball 7 to the side-view image taker 22. In this way, the same object distance can be obtained for both the top-view image taker 21 and the side-view image taker 22 while saving the space for installing the table 11.

According to the preferred form shown, the control unit 3 is electrically connected to the image taking device 2 to control the image taking time of the top-view image taker 21 and the side-view image taker 22 and to control on/off of the first and second parallel light sources 23 and 24, so that each of the first and second parallel light sources 23 and 24 flickers at a high frequency. Furthermore, the control unit 3 can analyze the images picked up by the image takers 21 and 22 to obtain functional parameters such as the moving paths of the ball hitting member 8 before and after hitting the ball 7, the flying speed of the ball 7, the inclination angle of the flying ball 7, and the backspin of the ball 7.

According to the preferred form shown, the sensor 4 is mounted on the holding seat 113 of the base 1 and coupled to the control unit 3. The sensor 4 detects the time before the ball hitting member 8 hits the ball 7, so that the image taking device 2 can precisely begin to pick up images at a beginning time through control by the control unit 3.

According to the preferred form shown, the swinging device 5 simulates the swinging posture of a man and holds the ball hitting member 8 to hit the ball 7 on the holding seat 113. In the most preferred form shown, the swinging device 5 is in the form of a robotic arm, and the ball hitting member 8 is in the form of a golf club. However, the ball hitting member 8 can be a racket for a tennis ball or a table tennis ball.

In use, while the swinging device 5 swings the ball hitting member 8 to hit the ball 7, the ball hitting member 8 passes through and activates the sensor 4 before hitting the ball 7. The sensor 4 sends a signal to the control unit 3 to activate the image taking device 2 to start to pick up images of the ball 7 hit by the ball hitting member 8. The images picked up by the image taking device 2 are sent back to the control unit 3, and the control unit 3 allows the user to read and to analyze the images for obtaining data of the test. The environment for taking images for the image taking device 2 is preferably a dark room to avoid interference from other light sources other than the first and second parallel light sources 23 and 24, assuring the quality of the images of the ball 7 and the ball hitting member 8.

Figure 4:
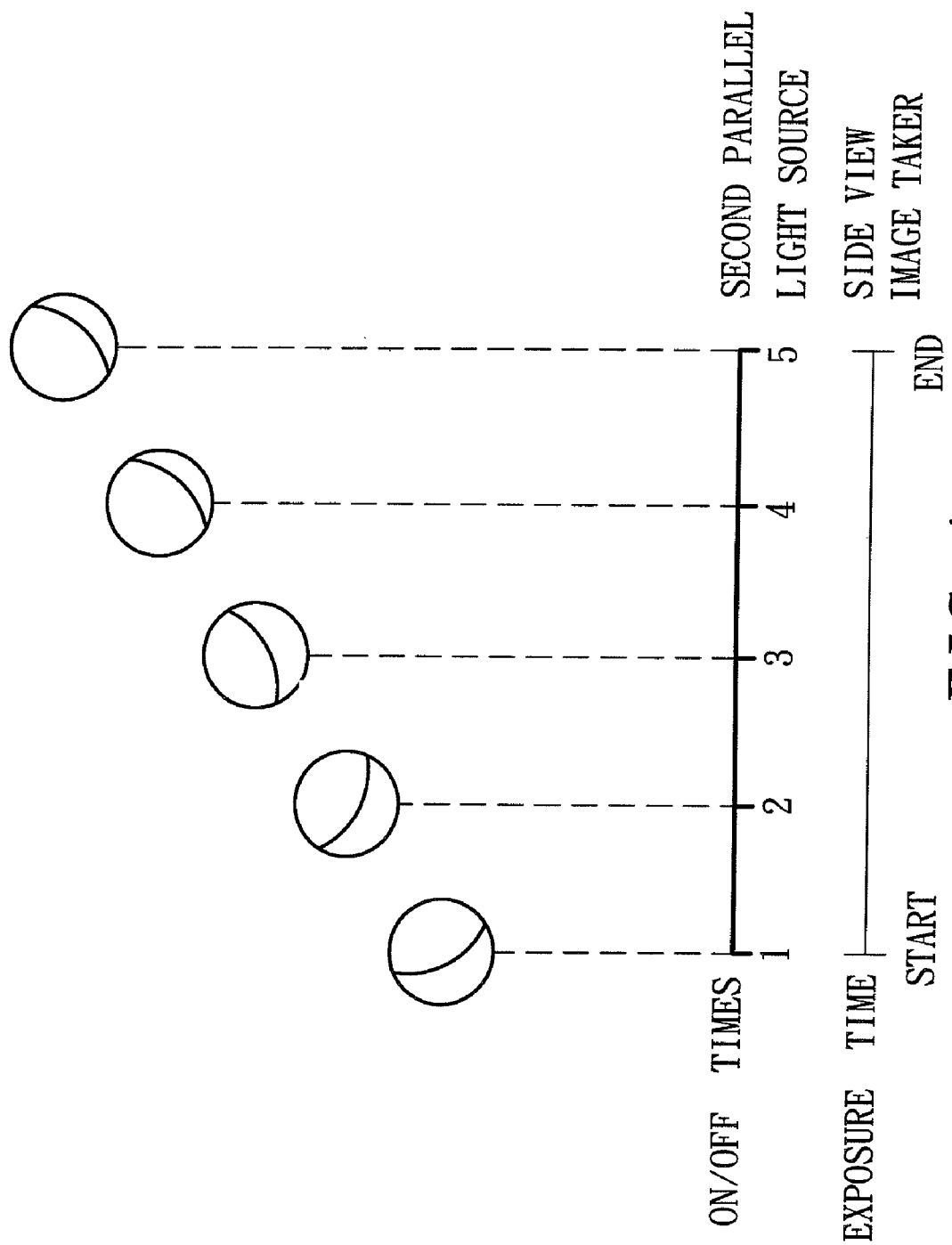
FIG. 4 shows images picked up by an image taking device of the performance test apparatus of FIG. 1.

During image taking by the image taking device 2, the shutters of the image takers 21 and 22 remain open (i.e., long exposure), and each of the first and second parallel light sources 23 and 24 flickers a plurality of times during the exposure time, so that different locations in the flying path of the ball 7 and different locations of the ball hitting member 8 in its moving path can be in the same picture. FIG. 4 shows different locations of the flying ball 7 taken by the side-view image taker 22, with five images of the ball 7 being picked up while the shutter of the side-view image taker 22 is open, and the second parallel light source 24 is turned on and off five times to provide light sources for the side-view image taker 22 five times. When the second parallel light source 24 is turned on for the first time, the image picked up by the side-view image taker 22 is the leftmost one of FIG. 4. The second to fifth times of turning on the second parallel light source 24 respectively obtain the second to fifth images from the left to the right of FIG. 4. On the other hand, when the first and second parallel light sources 23 and 24 are turned off, the images taken by the image takers 21 and 22 are all black, if the environment is a dark room. This makes the images of the ball 7 more clear. The ball 7 can have a mark on its sphere. The mark preferably extends along the circumference of the ball 7, providing a reference line for judging the spinning angle of the ball 7 after hitting.

To enhance the quality of the images of the ball 7 and the ball hitting member 8 taken by the image takers 21 and 22, the backdrop 6 is preferably a black velvet including a top-view backcloth 61 and a side-view backcloth 62. The top-view backcloth 61 is placed on the holding seat 113 of the base 1 so that the ball 7 is between the top-view image taker 21 and the top-view backcloth 61. The side-view backcloth 62 faces the frame 12 of the base 1 so that the ball 7 is between the side-view backcloth 62 and the second parallel light sources 24.

Figure 5:
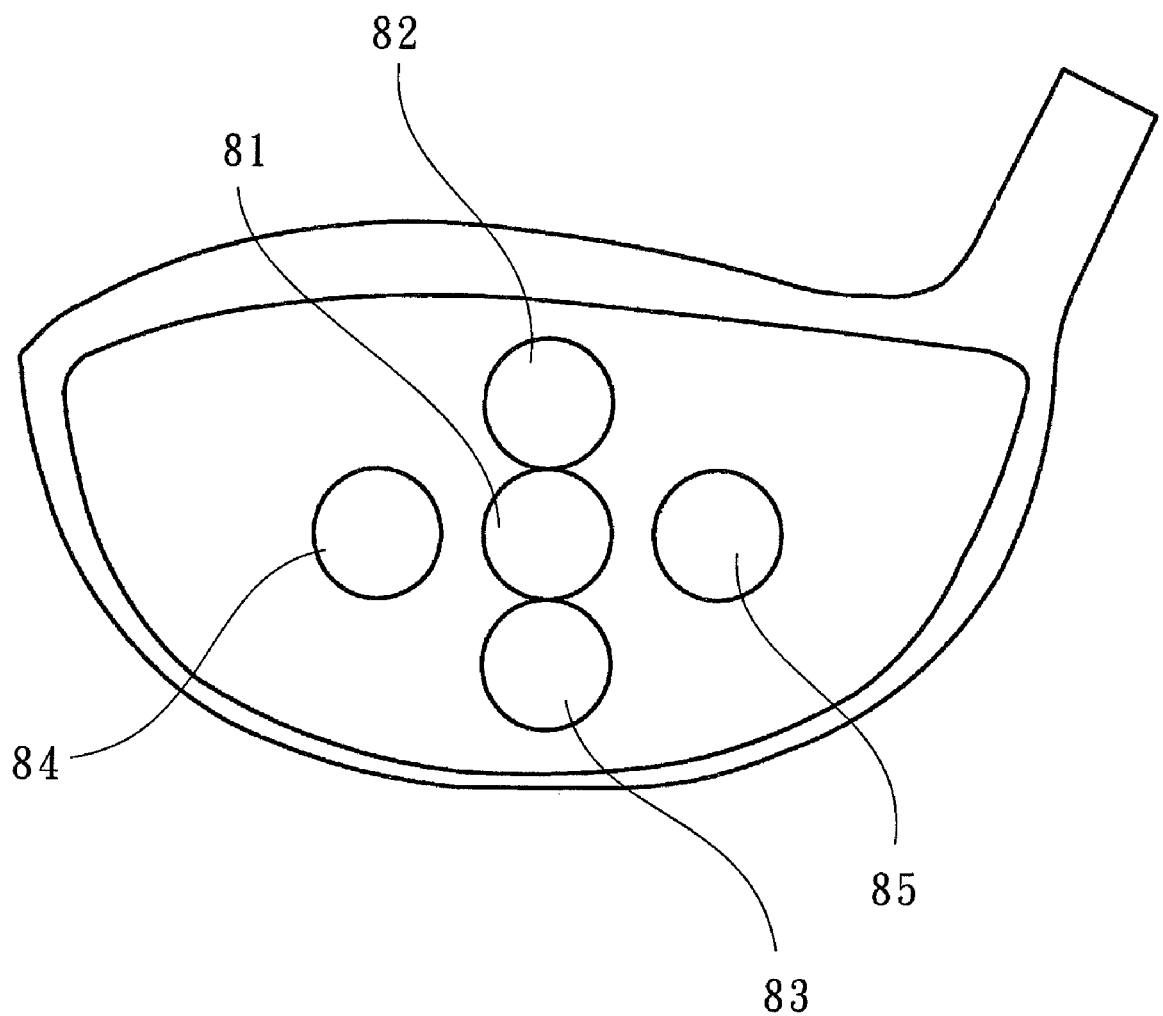
FIG. 5 shows distribution of a striking face of the performance test apparatus of FIG. 1.

FIG. 5 shows a striking face of a golf club. To assist in analysis of the sweet area of the striking face, five striking sections including left, right, upper, lower, and central striking sections 84, 85, 82, 83 and 81 are defined in the striking face. Each center of the upper and lower striking sections 82 and 83 is spaced from a center of the central striking section 81 by 10 mm, and each center of the left and right striking sections 84 and 85 is spaced from the center of the central striking section 81 by 20 mm. Each of the striking sections 81-85 repeatedly hits the ball 7 ten times to obtain the data of the speed, inclination angle, and backspin of the ball 7. The data obtained from hitting the ball 7 with the central striking section 81 is shown in Table 1. The data obtained from hitting the ball 7 with the left or right striking section 84, 85 is shown in Table 2. The data obtained from hitting the ball 7 with the upper or lower striking sections 82 and is shown in Table 3.

TABLE 1

| club head speed | ball speed (m/s) | inclination angle | backspin (RPM) | ball speed (m/s) | inclination angle | backspin (RPM) |
|---|---|---|---|---|---|---|
| | No. 1 club | | | No. 2 club | | |
| 40 m/s | 55.28 | 14.5 | 3474 | 54.98 | 14.0 | 3295 |
| 45 m/s | 60.20 | 18.3 | 4165 | 58.30 | 16.6 | 4359 |
| 50 m/s | 64.32 | 19.0 | 5332 | 66.43 | 17.6 | 5141 |
| | No. 3 club | | | No. 4 club | | |
| 40 m/s | 54.34 | 14.7 | 3831 | 56.35 | 15.4 | 3142 |
| 45 m/s | 56.31 | 15.7 | 4664 | 61.49 | 15.6 | 4442 |
| 50 m/s | 65.51 | 17.5 | 4853 | 63.61 | 18.2 | 5652 |

TABLE 2

| club head speed | striking section | ball speed (m/s) | inclination angle | backspin (RPM) | ball speed (m/s) | Inclination angle | backspin (RPM) |
|---|---|---|---|---|---|---|---|
| | | No. 1 club | | | No. 2 club | | |
| 40 m/s | left | 54.66 | 14.9 | 3193 | 54.73 | 14.6 | 2835 |
| | right | 52.57 | 15.3 | 2938 | 53.41 | 14.5 | 2809 |
| 45 m/s | left | 58.67 | 18.1 | 4248 | 60.57 | 17.4 | 4609 |
| | right | 57.17 | 17.0 | 3998 | 56.76 | 17.5 | 4386 |
| 50 m/s | left | 65.69 | 19.2 | 5588 | 65.08 | 17.7 | 4662 |
| | right | 62.48 | 19.4 | 5316 | 58.78 | 17.1 | 4598 |
| | | No. 3 club | | | No. 4 club | | |
| 40 m/s | left | 56.45 | 16.0 | 3678 | 52.22 | 16.1 | 3499 |
| | right | 50.32 | 14.9 | 3474 | 53.23 | 14.3 | 3218 |
| 45 m/s | left | 59.96 | 17.0 | 4331 | 59.95 | 17.1 | 4553 |
| | right | 57.58 | 17.0 | 4248 | 57.62 | 16.5 | 3804 |
| 50 m/s | left | 63.65 | 17.2 | 5236 | 68.11 | 18.7 | 4757 |
| | right | 64.78 | 17.5 | 4758 | 61.71 | 17.0 | 4310 |

TABLE 3

| club head speed | striking section | ball speed (m/s) | inclination angle | backspin (RPM) | ball speed (m/s) | inclination angle | backspin (RPM) |
|---|---|---|---|---|---|---|---|
| | | No. 1 club | | | No. 2 club | | |
| 40 m/s | upper | 52.03 | 20.4 | 3729 | 55.83 | 15.2 | 3661 |
| | lower | 52.77 | 14.2 | 3794 | 54.41 | 12.4 | 3857 |
| 45 m/s | upper | 59.67 | 22.3 | 4623 | 59.69 | 18.7 | 4054 |
| | lower | 59.71 | 16.0 | 4859 | 57.66 | 15.5 | 4872 |
| 50 m/s | upper | 63.68 | 21.2 | 4789 | 65.87 | 19.2 | 4854 |
| | lower | 65.72 | 16.5 | 5715 | 62.28 | 16.2 | 5053 |
| | | No. 3 club | | | No. 4 club | | |
| 40 m/s | upper | 57.41 | 17.6 | 2555 | 54.02 | 16.2 | 2758 |
| | lower | 54.12 | 9.7 | 3270 | 53.62 | 10.7 | 3729 |
| 45 m/s | upper | 60.36 | 19.1 | 4553 | 60.44 | 19.5 | 3693 |
| | lower | 60.13 | 13.9 | 4673 | 58.96 | 14.0 | 4609 |
| 50 m/s | upper | 64.43 | 20.9 | 4821 | 62.76 | 20.9 | 4885 |
| | lower | 62.22 | 15.1 | 5460 | 64.79 | 14.9 | 5651 |

The faster the speed of the ball 7 is, the farther the ball 7 flies. The larger the inclination angle and the backspin, the longer the ball 7 stays in the air. According to the tables, when the golf club hits the ball 7 with the central striking section 81, No. 1 club has a larger inclination angle when the speed is 45 m/s or 50 m/s, whereas No. 4 club has a larger speed and larger inclination angle when the speed is 40 m/s. When the golf club hits the ball 7 with the left or right striking section 84, 85, No. 1 club has a larger speed, larger inclination angle, and larger backspin when the speed is 50 m/s. When the golf club hits the ball 7 with the upper or lower striking section 82, 83, No. 1 club has a larger speed, larger inclination angle, and larger backspin when the speed is 40/s or 50 m/s. Thus, it can be inferred that No. 1 club is suitable for professionals, while No. 4 club is suitable for non-professionals.

Figure 6:
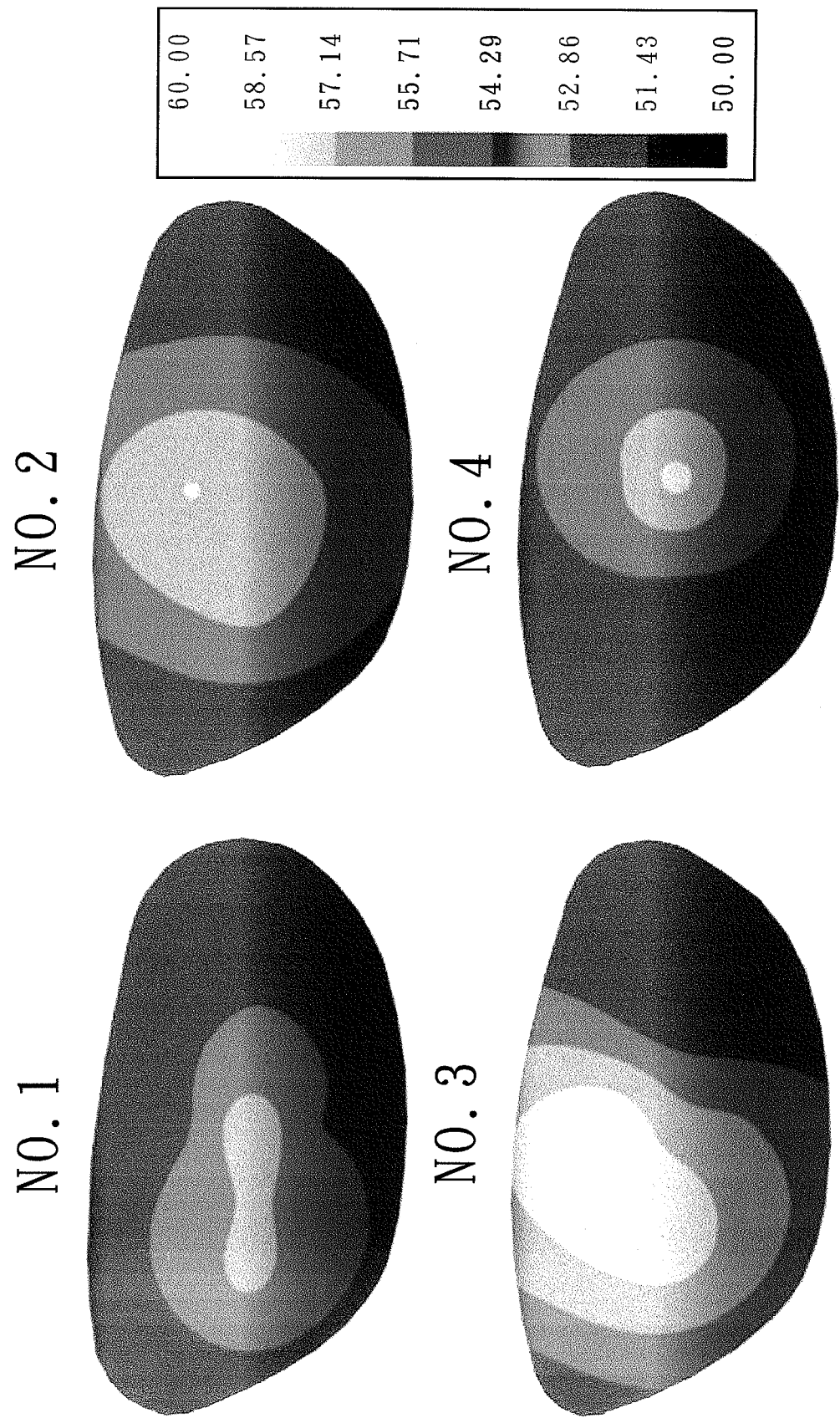
FIG. 6 shows distribution of the sweet areas of golf clubs striking at a speed of 40 m/s.
Figure 7:
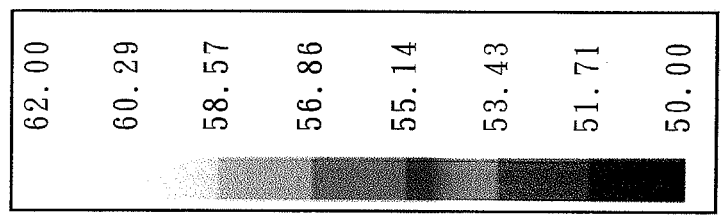
FIG. 7 shows distribution of the sweet areas of golf clubs striking at a speed of 45 m/s.
Figure 7:
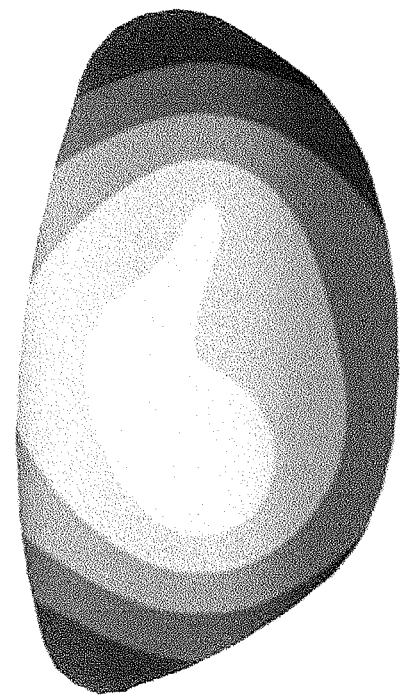
Figure 7:
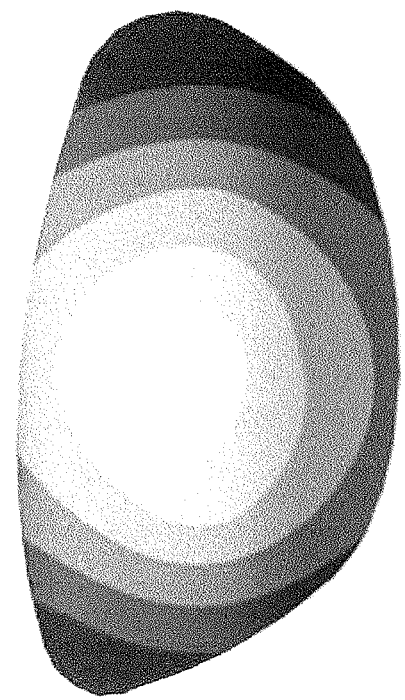
Figure 7:
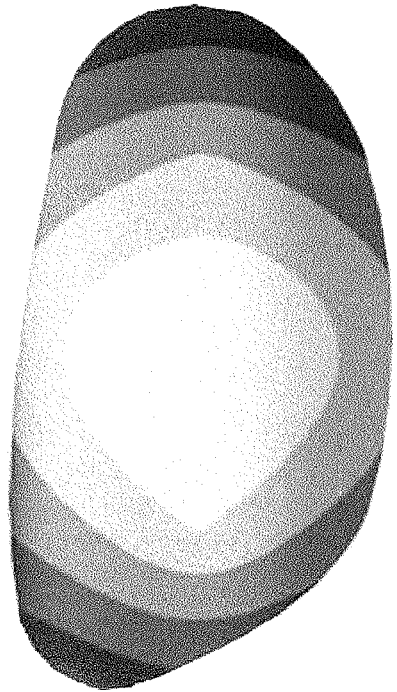
Figure 7:
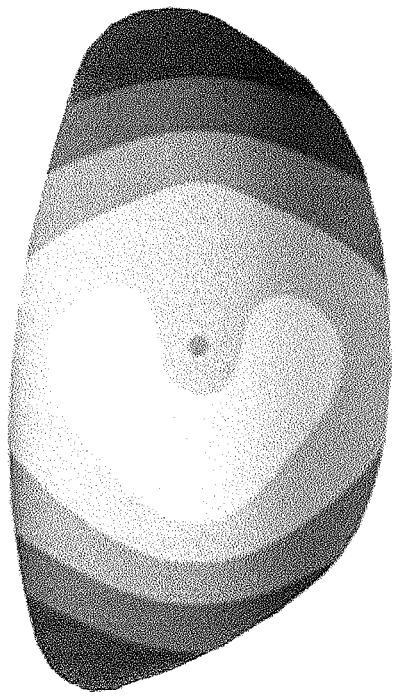
Figure 8:
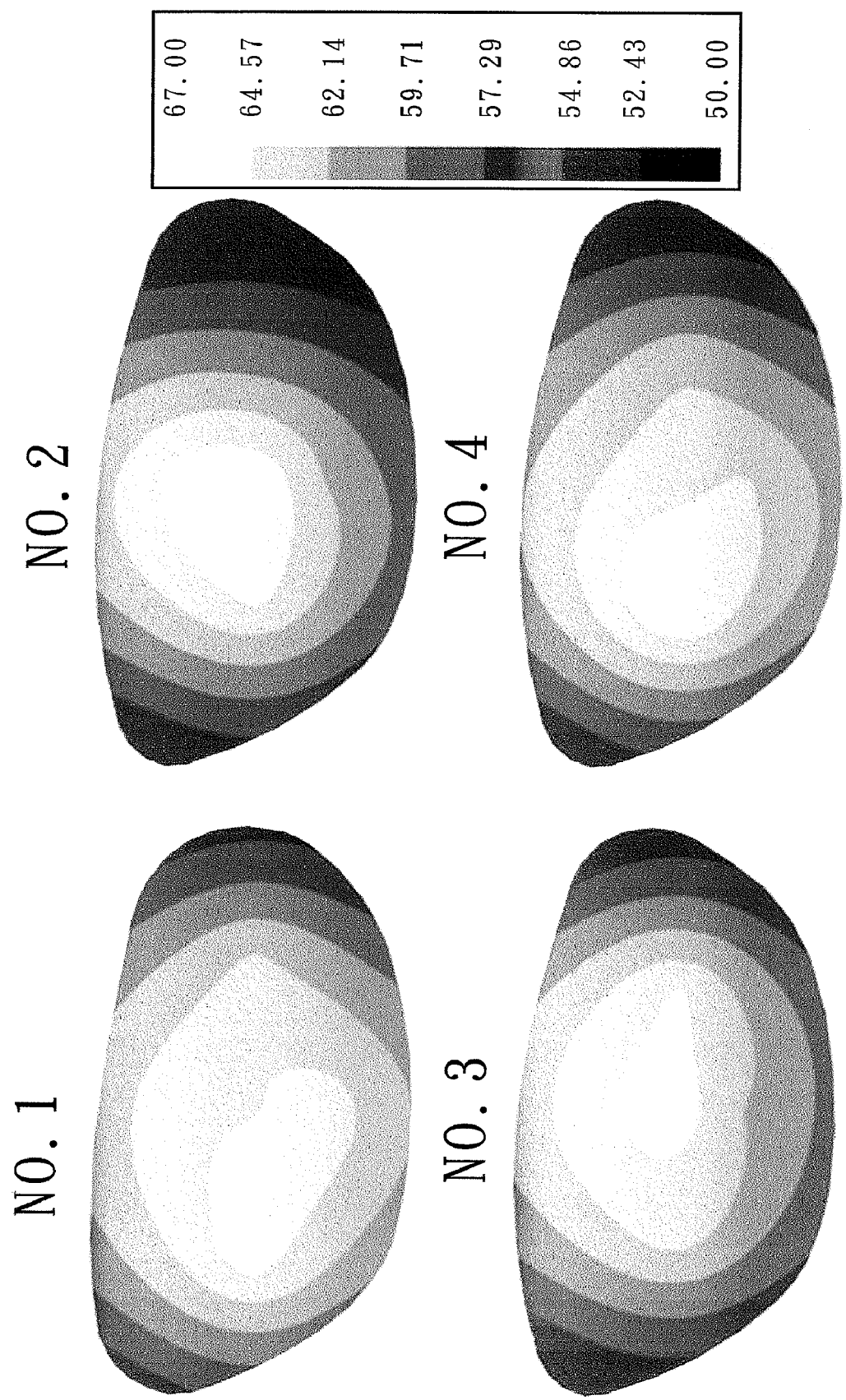
FIG. 8 shows distribution of the sweet areas of golf clubs striking at a speed of 50 m/s.

The distribution of speeds is depicted on the striking faces of No. 1 to No. 4 clubs after data analysis of the images to identify the sweet areas. FIG. 6 shows distribution of the sweet areas when the club head hits the ball 7 at the speed of 40 m/s. FIG. 7 shows distribution of the sweet areas when the club head hits the ball 7 at the speed of 45 m/s. FIG. 8 shows distribution of the sweet areas when the club head hits the ball 7 at the speed of 50 m/s. It can be seen that the sweet areas of No. 1 club and No. 4 club have more uniform distribution. However, No. 1 club has a larger sweet area.

As can be seen from FIGS. 6-8, the performance of No. 1 club in the inclination angle and the speed is better than the other clubs. Although the speed of No. 4 club is larger than No. 1 club by 2-3 m/s, the sweet area of No. 4 club is smaller than No. 1 club. Thus, it can be inferred that No. 1 club is better and performs excellent in high speed tests. It is, thus, proven that the performance test apparatus according to the preferred teachings of the present invention can carry out tests of performance of golf clubs and distribution of the sweet areas.

The performance test apparatus according to the preferred teachings of the present invention utilizes two first parallel light sources 23 to provide a parallel, uniform light source for the top-view image taker 21 and the second parallel light source 24 to provide parallel, uniform light source for the side-view image taker 22, so that the image taking device 2 can pick up images of the ball 7 hit by the ball hitting member 8, with the first and second parallel light sources 23 and 24 providing uniform illumination for the ball 7 and the ball hitting member 8. Furthermore, the control unit 3 controls the first and second parallel light sources 23 and 24 to flicker at high frequency, so that the image takers 21 and 22 have longer exposure time to obtain the photographing effect of a high-speed camera utilizing a high-speed shutter. Thus, the performance test apparatus according to the preferred teachings of the present invention enhances the measuring accuracy and can be manufactured at low costs.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A performance test apparatus comprising:
    a control unit;
    a base including a table and a frame mounted to the table, with the table including a fixed seat, a movable seat movably mounted to the fixed seat, and a holding seat movably mounted to the movable seat; and
    an image taking device including at least one image taker and at least one parallel light source, with at least one image taker being movably mounted to the frame and electrically connected to the control unit, with said at least one parallel light source facing the table and electrically connected to the control unit,
    with said at least one parallel light source including a plurality of spot light sources, with the control unit controlling on/off of said at least one parallel light source, so that said at least one parallel light source flickers at a high frequency.

2. The performance test apparatus as claimed in claim 1, further comprising: a swinging device and a sensor, with the sensor mounted on the table and coupled to the control unit.

3. The performance test apparatus as claimed in claim 1, with the frame of the base including two posts and first, second, and third beams, with each of the two posts including a first end fixed to a side of the fixed seat of the table, with each of the two posts further including a second end, with the second ends of the two posts fixed to two ends of the first beam, with the second beam including an end movably mounted to the first beam, with the third beam mounted between the first beam and the fixed seat, and with the third beam including two ends fixed to the two posts.

4. The performance test apparatus as claimed in claim 3, with the at least one image taker including a top-view image taker mounted by a first coupling member to the second beam.

5. The performance test apparatus as claimed in claim 4, with said at least one parallel light source including two parallel light sources mounted by two connecting members to the first coupling member, and with the two parallel light sources on two sides of the top-view image taker.

6. The performance test apparatus as claimed in claim 3, with at least one image taker including a side-view image taker, with said at least one parallel light source including a parallel light source, with the side-view image taker and the parallel light source movably mounted by a second coupling member to the third beam.

7. The performance test apparatus as claimed in claim 6, further comprising: a reflective mirror mounted below the side-view image taker.

8. The performance test apparatus as claimed in claim 3, further comprising: at last one backdrop facing said at least one parallel light source.

9. The performance test apparatus as claimed in claim 8, with the backdrop including a top-view backcloth mounted on the holding seat of the base.

10. The performance test apparatus as claimed in claim 8, with the backdrop including a side-view backcloth facing the frame of the base.

* * * * *